(12) United States Patent
Miladinovic et al.

(10) Patent No.: US 9,195,022 B2
(45) Date of Patent: Nov. 24, 2015

(54) STAND FOR A MEDICAL DEVICE

(71) Applicant: Carl Zeiss Meditec AG, Jena (DE)

(72) Inventors: Tabea Miladinovic, Aalen (DE); Luisa Bofinger, Kranenburg (DE)

(73) Assignee: Carl Zeiss Meditec AG, Jena (DE)

( * ) Notice: Subject to any disclaimer, the term of this patent is extended or adjusted under 35 U.S.C. 154(b) by 322 days.

(21) Appl. No.: 13/959,401

(22) Filed: Aug. 5, 2013

(65) Prior Publication Data
US 2013/0313382 A1 Nov. 28, 2013

Related U.S. Application Data

(63) Continuation of application No. PCT/EP2012/050540, filed on Jan. 16, 2012.

(30) Foreign Application Priority Data

Feb. 3, 2011 (DE) .......... 10 2011 003 589

(51) Int. Cl.
*A47F 5/00* (2006.01)
*G02B 7/00* (2006.01)
*A61B 19/00* (2006.01)
(Continued)

(52) U.S. Cl.
CPC . *G02B 7/00* (2013.01); *A61B 19/26* (2013.01); *F16M 11/10* (2013.01); *F16M 11/2064* (2013.01); *F16M 11/2092* (2013.01); *F16M 11/24* (2013.01); *F16M 13/027* (2013.01);
(Continued)

(58) Field of Classification Search
CPC .......... G02B 7/00; G02B 7/001; A61B 19/26; A61B 2019/266; F16M 11/10; F16M 11/2064; F16M 11/2092; F16M 11/24; F16M 13/027; F16M 2200/063

USPC .......... 248/124.1, 125.7, 278.1, 280.11, 248/281.11
See application file for complete search history.

(56) References Cited

U.S. PATENT DOCUMENTS 3,762,797 A 10/1973 Heller
4,548,373 A * 10/1985 Komura ................. A61B 6/105
188/171

(Continued)

FOREIGN PATENT DOCUMENTS

DE 103 31 094 A1 2/2005
DE 10 2004 063 606 A1 7/2006
FR 2 492 014 A2 4/1982

OTHER PUBLICATIONS

International Search Report dated Mar. 7, 2012 of international application PCT/EP2012/050540 on which this application is based.
(Continued)

*Primary Examiner* — Gwendolyn Baxter
(74) *Attorney, Agent, or Firm* — Walter Ottesen P.A.

(57) ABSTRACT

The invention relates to a stand for a medical device. The stand includes a first support arm and a second support arm, which is connected to the first support arm via a first joint connection having a first degree of freedom of motion and on which the medical device can be held. The first joint connection has a first switching device, which can be put into a first switching state and into a second switching state, wherein, in the first switching state, the first degree of freedom of motion is blocked or disabled and wherein, in the second switching state, the first degree of freedom of motion is open or enabled.

21 Claims, 11 Drawing Sheets

(51) Int. Cl.
*F16M 11/10* (2006.01)
*F16M 11/20* (2006.01)
*F16M 11/24* (2006.01)
*F16M 13/02* (2006.01)

(52) U.S. Cl.
CPC ........... *G02B 7/001* (2013.01); *A61B 2019/266* (2013.01); *F16M 2200/063* (2013.01)

(56) References Cited

U.S. PATENT DOCUMENTS

| | | | | |
|---|---|---|---|---|
| 5,170,790 | A * | 12/1992 | Lacoste | A61B 8/12 128/122.1 |
| 6,364,268 | B1 | 4/2002 | Metelski | |
| 6,514,239 | B2 * | 2/2003 | Shimmura | A61B 19/26 600/427 |
| 7,189,246 | B2 * | 3/2007 | Otsuka | A61B 19/0256 600/102 |
| 7,412,776 | B2 * | 8/2008 | Iikubo | A61B 8/4218 248/280.11 |
| 2002/0014562 | A1 * | 2/2002 | Twisselmann | A61B 19/26 248/123.11 |
| 2004/0246469 | A1 | 12/2004 | Hirose | |
| 2005/0117207 | A1 * | 6/2005 | Haisch | A61B 19/52 359/381 |
| 2005/0230584 | A1 | 10/2005 | Kuhn | |
| 2010/0204578 | A1 | 8/2010 | Schmidt et al. | |

OTHER PUBLICATIONS

English translation and Office action of the German Patent Office dated Jul. 19, 2011 in German patent application 10 2011 003 589.3 on which the claim of priority is based.

* cited by examiner

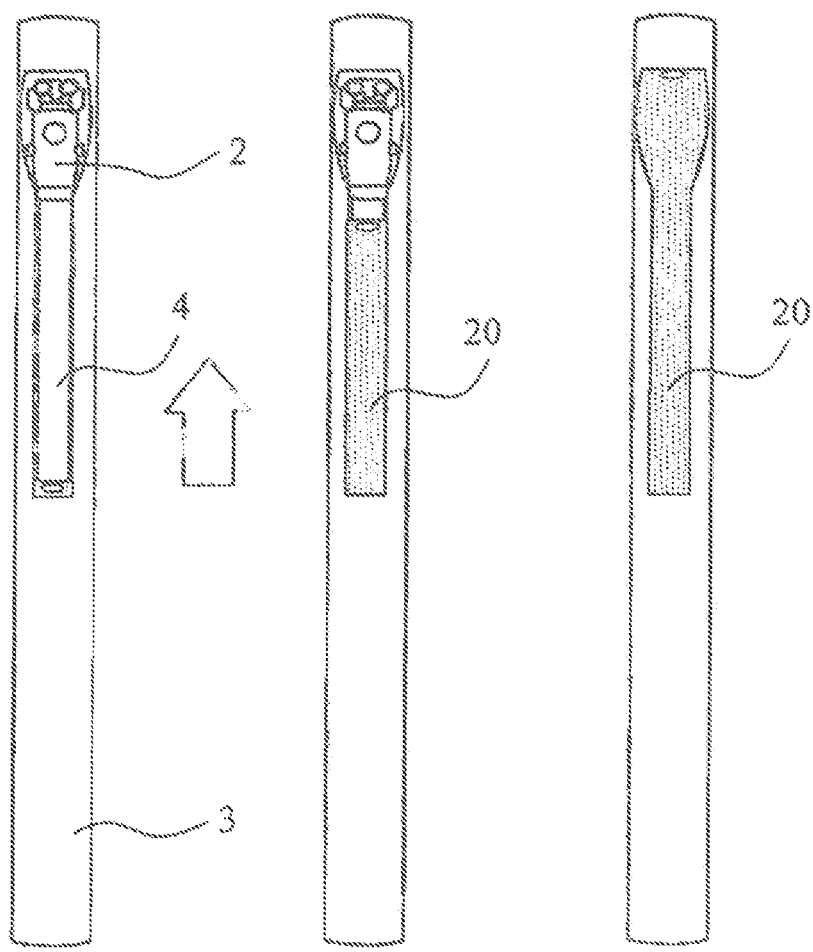

STAND FOR A MEDICAL DEVICE

CROSS REFERENCE TO RELATED APPLICATIONS

This application is a continuation application of international patent application PCT/EP2012/050540, filed Jan. 16, 2012, designating the United States and claiming priority from German application 10 2011 003 589.3, filed Feb. 3, 2011, and the entire content of both applications is incorporated herein by reference.

FIELD OF THE INVENTION

The invention relates to a stand for a medical device, with the stand including a first support aria and a second support arm. The second support arm is connected to the first support arm via a first joint connection with at least one degree of freedom of motion. The medical device can be held on the second support arm.

BACKGROUND OF THE INVENTION

Medical procedures cannot be contemplated without stands of the type mentioned above. During a treatment or a surgical procedure, different medical devices have to be positioned in space in such a way that all required functions are available and, at the same time, ergonomic work is possible. In this context, surgical microscopes, cameras, treatment or surgical instruments, screens for displaying videos and/or data and monitoring instruments are mentioned as examples of medical devices. For these, use is often made of stands with two or more support arms which are connected to one another via joint connections with each having one or more degrees of freedom of motion in such a way that a medical device attached to a support arm can be positioned within a defined workspace of the stand. Here, a workspace of the stand should be understood to mean the totality of all positions and angular positions which the stand and the medical device can assume in space.

U.S. Pat. No. 6,364,268 discloses a stand for a surgical microscope. The stand has a plurality of support arms connected in series, which, if required, can be aligned in a parked position.

A situation which often occurs in medical operation is that medical devices are only required temporarily. This particularly holds true in the case of surgical microscopes, which are often only required during specific treatment steps. Between the treatment steps or after completion of the treatment, the treatment space available to the medical practitioner, that is, the free space in the surroundings of the treatment location on the patient, is unnecessarily restricted by the medical device.

SUMMARY OF THE INVENTION

An object of the present invention is to provide a stand for a medical device, which stand can easily be transferred into a rest position wherein the treatment space is less confining. The stand should preferably assume the rest position if the medical device is not required during the treatment or surgical procedure.

The stand of the invention is for a medical device. The stand includes: a first, support arm; a second support arm configured to accommodate the medical device thereon; a first joint connection configured to connect the second support arm to the first support arm with a first degree of freedom of motion; the first joint connection having a first switching device configured to be transferable into a first switching state wherein the first degree of freedom of motion is disabled and into a second switching state wherein the first degree of freedom of motion is enabled; the first joint connection being configured to have a second degree of freedom of motion; and, the second degree of freedom of motion being enabled in the first switching state of the first switching device and the second degree of freedom of motion being disabled in the second switching state of the first switching device.

According to the invention, the first joint connection has a first switching device, which can be transferred into a first switching state and into a second switching state, wherein, in the first switching state, the first degree of freedom of motion is blocked or disabled and wherein, in a second switching state, the first degree of freedom of motion is open or enabled. As a result of this, it is possible to provide an additional degree of freedom of motion for the transition from a work position into the rest position by transferring the first switching device into the second switching state. Here, a work position should be understood to mean a position of the stand, in which the stand is placed in such a way that the medical device can be employed by the medical practitioner during the treatment or surgical procedure. The switching device according to the invention makes it easier to transfer the stand from the work position into the rest position.

In one embodiment of the invention, the first switching device comprises means via which the first switching device can only be switched into the second switching state if a longitudinal axis of the first support arm and a longitudinal axis of the second support arm are arranged in one plane. The provision of an additional degree of freedom of motion of the stand for the transition from the work position into the rest position is therefore only possible from specific positions of the stand in the workspace. Inadvertent switching of the switching device into a different switching state is prevented in large parts of the workspace, as a result of which the work safety is improved.

In a further embodiment of the invention, the first degree of freedom of motion of the first joint connection is formed as a translational degree of freedom along the longitudinal axis of the first support arm. Hence, the second support arm can be moved along the first support arm during the transition from, the work position into the rest position and, in particular, also be pushed, into or over the first support arm, at least in parts.

In a further embodiment of the invention, the first degree of freedom of motion of the first joint connection is formed as a rotational degree of freedom about a first rotational axis. This allows the second support arm to be folded in the direction onto the first support arm during the transition from the work position into the rest position.

In a further embodiment of the invention, the first joint connection has a second degree of freedom of motion which, in the first switching state of the first switching device, is open and, in the second switching state of the first switching device, is blocked. As a result, the second degree of freedom of motion of the stand is blocked during the transition from the work position into the rest position. This allows a movement trajectory of the stand to be influenced during the transition from the work position into the rest position. In particular, it is possible to limit the amount of workspace available to the stand during the transition.

In a further embodiment, the second degree of freedom of motion of the first joint connection is configured as a rotational degree of freedom about a second rotational axis. As a result, it is possible to influence in many ways the workspace available for the transition between the work position and the rest position. The second rotational axis is preferably aligned skew or orthogonal with respect to the first rotational axis.

In a further embodiment of the invention, the first support arm is configured as a parallelogram structure such that a hinge plane of the first joint connection on the first support arm is guided parallel to a hinge plane of the first support arm on the opposite end of the first support arm.

In a further embodiment of the invention, the first support arm is connected to a main body of the stand via a second joint connection with a rotational degree of freedom about a third rotational axis. This provides a further actuation option for influencing the workspace during the transition from the work position into the rest position.

In a further embodiment of the invention, the first rotational axis of the first joint connection and the third rotational axis of the second joint connection are arranged parallel to one another. As a result, the first support arm and the second support arm can be folded onto one another in a particularly space-saving manner and be removed from the treatment space for the medical practitioner.

In a further embodiment of the invention, the second joint connection comprises a second switching device, which can be put into a third switching state and into a fourth switching state, wherein, in the third switching state, the rotational degree of freedom about the third rotational axis is blocked and wherein, in the fourth switching state, the rotational degree of freedom about the third rotational axis is open. Hence a further degree of freedom of motion is provided in the fourth switching state in order to influence the workspace during the transition of the stand from the first position into the rest position. In particular, the additional degree of freedom of motion renders it possible to remove the first support arm and the second support arm in a particularly space-saving manner from the treatment space for the medical practitioner by virtue of resting the support arms against an adjoining structure of the stand.

In a further embodiment of the invention, the first switching device and the second switching device are coupled. A coupling device is preferably configured in such a way that the rotational, degree of freedom of the second joint connection is blocked if the first degree of freedom of motion of the first joint connection is blocked and the rotational degree of freedom of the second joint connection is open if the first degree of freedom of motion of the first joint connection is open. As a result, the first switching state of the first switching device is coupled to the third switching state of the second switching device and the second switching state of the first switching device is coupled to the fourth switching state of the second switching device. By transferring the switching devices into the second and fourth switching state, respectively, the workspace of the stand available during a transition from the first position into the rest position can be configured in an optimum manner, while, in the case of the switching devices being switched into the first and third switching state, respectively, the workspace of the stand required for the medical treatment is available.

In a further embodiment of the invention, the stand comprises a switchable coupling between the main body, the first support arm and the second support arm, by means of which a movement of the first support arm relative to the main body is coupled to a movement of the second support arm relative to the first support arm. The workspace available during the transition of the stand from the work position into the rest position is further restricted as a result of the coupling. In particular, the coupling can be configured in such a way that the first support arm and the second support arm of the stand can only be transferred from the work position into the rest position along a defined trajectory. By way of example, the coupling between the main body and the first support arm and the second support arm can be configured mechanically via toothed wheels, gears or Bowden-cable connections or electromotively, hydraulically, magnetically or pneumatically.

In a further embodiment of the invention, the main body has a cavity in which the first support arm and the second support arm can be held in a parked position. Here, the parked position should be understood to mean a particular rest position of the stand in which the support arms are housed in a particularly space-saving and protected manner. The risk of an inadvertent collision with the support arms and a medical device attached thereto is reduced in the parked position. The first switching device is preferably put into the second switching state when the stand is positioned in the parked position.

In a further embodiment of the invention, the stand comprises a locking device, by means of which the first support arm and the second support arm can be locked relative to the main body in the parked position. This prevents the support arms from falling out of the main body in the parked position. Here, the locking device can be configured, as a force-fit or interlocking connection, which can be released by simple means.

In a further embodiment of the invention, the stand comprises a holding device, by means of which the first support arm and the second support arm are held in a ready position. Here, a ready position constitutes a further rest position, in which the stand with a medical device attached thereto is positioned outside of the treatment space for the medical practitioner, but in reach of the medical practitioner or the operating staff. The stand is held in the ready position, from which the medical practitioner or the operating staff can move it into the work position in an ergonomically expedient fashion, by means of the holding device.

In a further embodiment of the invention, the first switching device is put into the second switching state in the ready position. Hence the stand can be moved out of the ready position only in the workspace set by the first switching device. It is particularly preferred for a second switching device also to be put into the fourth switching state in the ready position such that a movement trajectory of the stand is determined in a defined fashion.

In a further embodiment of the invention, the holding device comprises an energy store which can, for example, be embodied in the form of a spring. A ready position can be set in a structurally simple manner by means of an energy store.

In a further embodiment of the invention, the holding device comprises a motor, which preferably has an electric design and is arranged between the main body and the first support arm and/or the second support arm. As a result, there is an alternative or complementary means for holding the stand in a ready position.

In a further embodiment, the stand comprises a closure device, by means of which an opening of the cavity can be closed. As a result of this, a medical device arranged on the stand is stowed in a protected fashion when not to use.

BRIEF DESCRIPTION OF THE DRAWINGS

The invention will now be described with reference to the drawings wherein:

FIG. 14 shows an embodiment of the stand with a closure device.

DESCRIPTION OF THE PREFERRED EMBODIMENTS OF THE INVENTION

Figure 1:
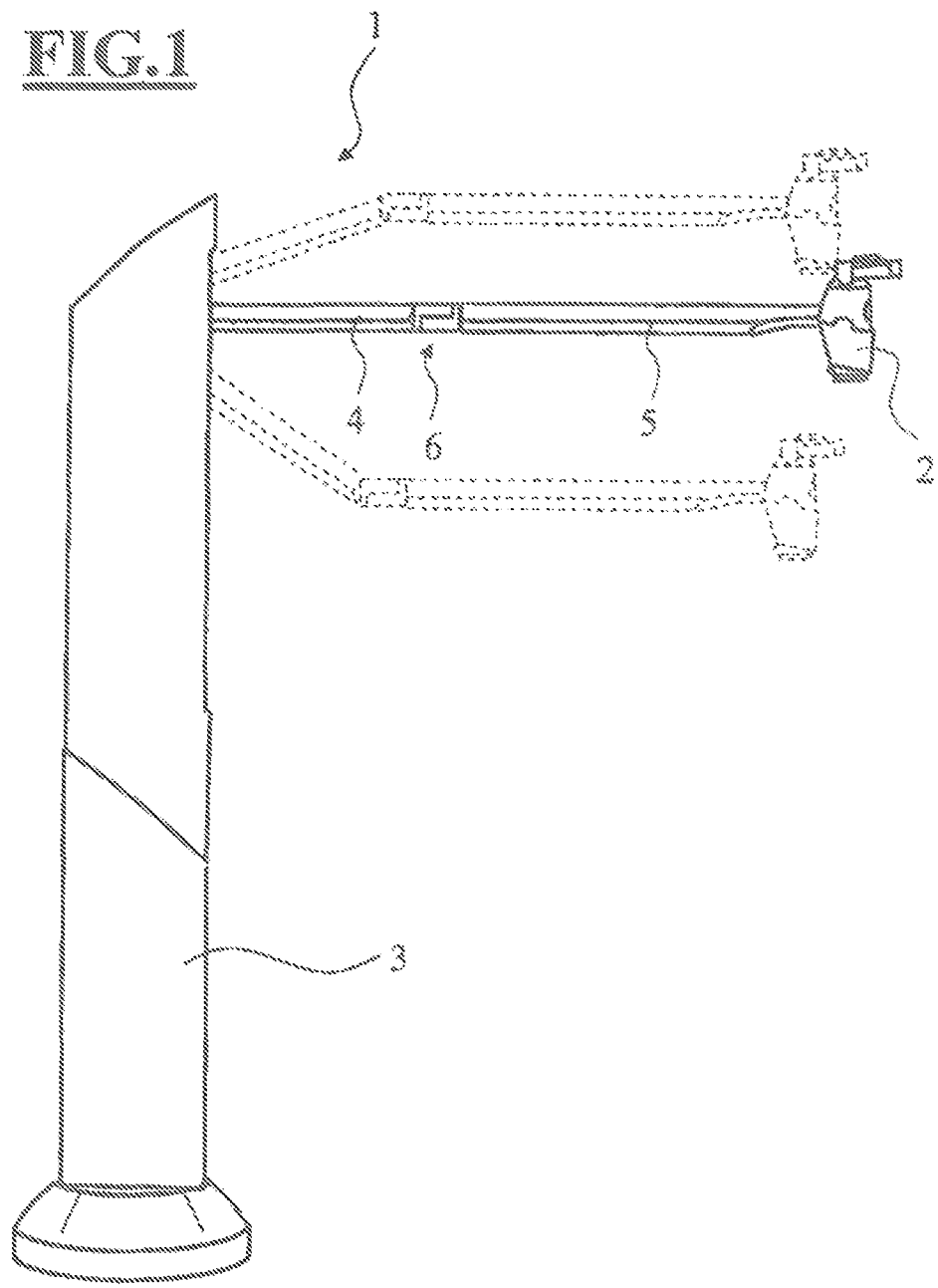
FIG. 1 shows a side view of various work positions of a stand according to the invention.
Figure 2:
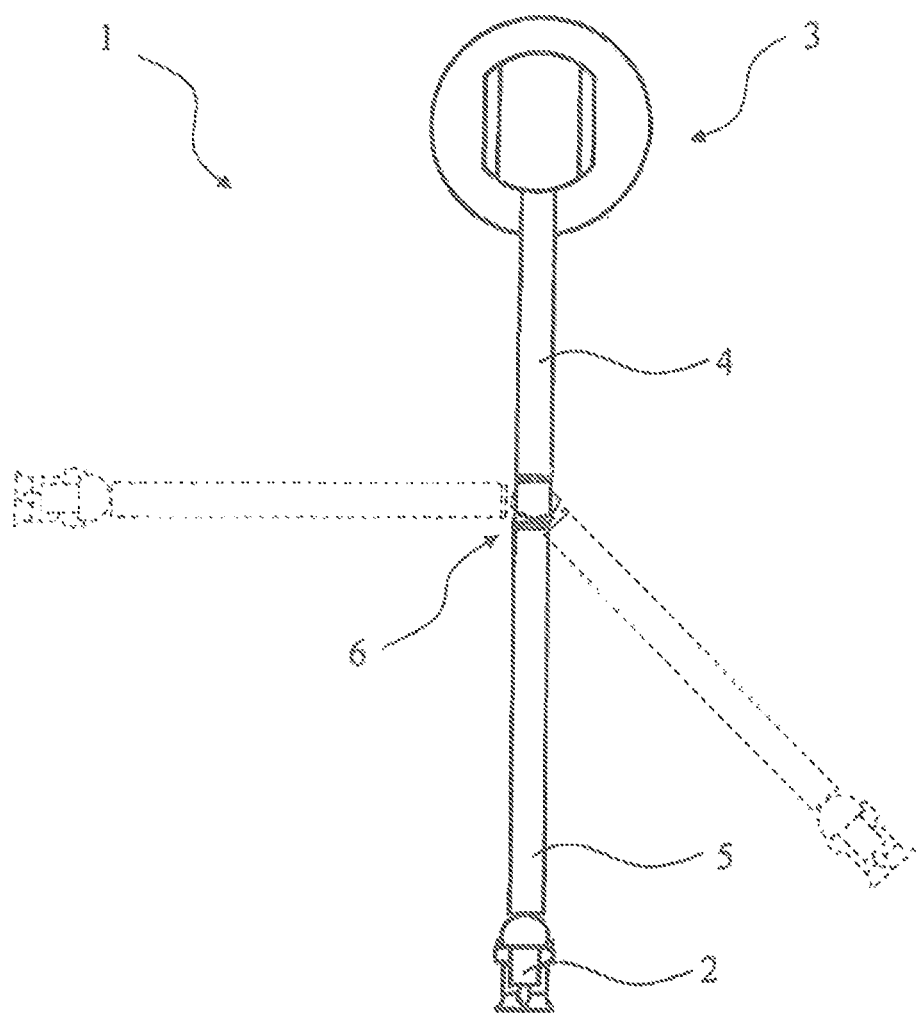
FIG. 2 is a plan view of various work positions of the stand shown in FIG. 1.

FIG. 1 and FIG. 2 illustrate a first embodiment of the stand 1 for holding a medical device in the form of a surgical microscope 2. The stand 1 is embodied as a floor stand, and comprises a main body 3 and a first, support arm 4 and a second support arm 5 which are connected to the main body in a kinematic chain.

The first support arm 4 and the second support arm 5 are interconnected by a first joint connection 6, which, as will be explained in more detail below, has at number of degrees of freedom of motion. A second joint connection 7 with at least one degree of freedom of motion is arranged between the main body 3 and the first support arm 4.

Arranged between the main body 3 and the floor or, alternatively, between the first support arm 4 and the main body 3, there is a swivel joint 21 (not shown in any more detail in FIG. 1) with a vertical rotational axis 22 such that either the main body 3 with the support arms (4, 5) attached thereto can be swiveled relative to the floor or the first support arm 4 with the second support arm 5 attached thereto can be swiveled relative to the main body 3 about the vertical rotational axis 22.

Arranged at the outer end of the second support arm 5 there is a receptacle device 9 for the surgical microscope 2, by means of which the surgical microscope can be attached to the second support arm. The connection between the surgical microscope 2 and the second support arm 5 preferably has a detachable design in this case. The receptacle device 9 can have a joint connection with one or more rotational and/or translational degrees of freedom of motion such that the surgical microscope 2 can be attached in a movable fashion, relative to the second support arm.

In this embodiment, the first support arm 4 is embodied as a parallelogram structure with horizontal rotational axes in the parallelogram joints 23 such that the second support arm 5 arranged on the first support arm 4 is displaced in parallel when pivoting the first support arm about the horizontal rotational axes of the parallelogram joints. The first support arm 4 therefore, as a parallelogram structure, comprises two kinematic chain elements, arranged parallel to one another, in this embodiment. However, without loss of generality, the first support arm can also be embodied as a single arm with only one kinematic chain element and joints at the respective ends of the single arm.

In FIG. 1 and FIG. 2, a work position of the stand is illustrated with full lines, in which work position the first support arm 4 is aligned perpendicular to a longitudinal axis of the main body 3 and the second support arm 5 is aligned in the continuation of the first support arm 4. Additionally, FIG. 1 and FIG. 2, using dashed lines, show further work positions into which the stand can be put. During a treatment or surgical procedure, it is often necessary to vary a position of the surgical microscope and the stand in order to be able to observe the particular region of surgery from the desired angle and from an appropriate distance. To this end, the treating medical practitioner has the following degrees of freedom available in this embodiment:

rotating the main body 3 about a vertical rotational axis 22 relative to the floor or, alternatively, rotating the first support arm 4 about a vertical rotational axis relative to the main body 3;

rotating the first support, arm 4 about one rotational axes of the parallelogram joints 23 relative to the main body 3;

rotating the second support arm 5 about a vertical axis relative to the first support arm 4; and, optionally rotating and/or translationally displacing the surgical microscope 2 relative to the second support arm 5 in the receptacle device.

The work positions shown with dashed and solid lines in FIG. 1 and FIG. 2 here are examples of positions into which the stand is put during a treatment of or surgical procedure on a patient.

Figure 3:
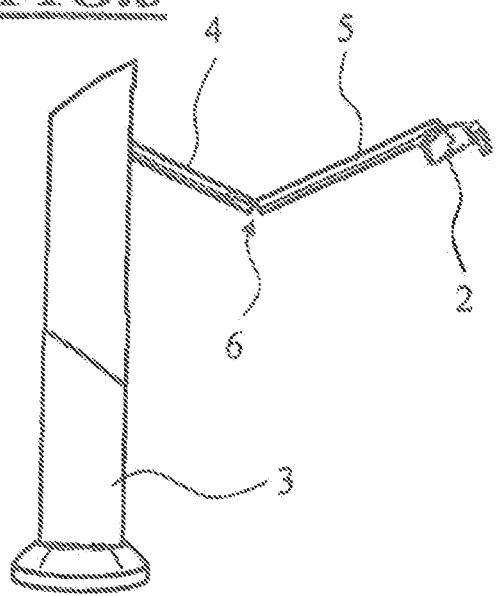
FIG. 3 shows the stand according to the invention in a transition position between a work position and a ready position.
Figure 4:
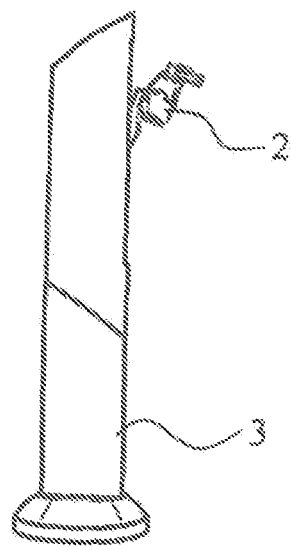
FIG. 4 shows the stand in a ready position.
Figure 5:
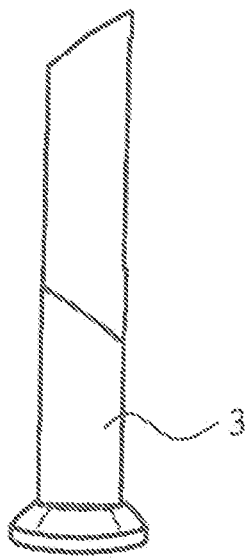
FIG. 5 shows the stand in a parked position.
Figure 6:
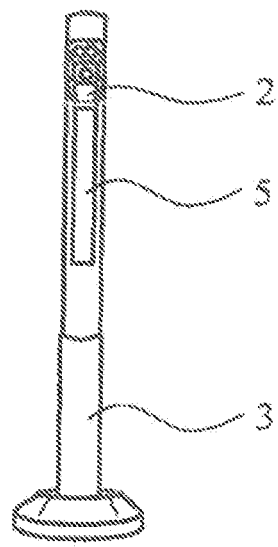
FIG. 6 shows a different view of the stand in accordance with FIG. 5.

FIG. 3 to FIG. 6 illustrate how the support arms of the stand 1 with the surgical microscope 2 situated thereon can be removed from the surgical region such that a larger treatment space is available to the medical practitioner. Here, treatment space refers to the space in the surroundings of the patient which the medical practitioner uses for the required surgical activity. In order to remove the support arms of the stand 1 and the surgical microscope 2 from the surroundings of the patient, an additional rotational degree of freedom about a first rotational axis 11 in the first joint, connection 6 is opened such that the second support arm 5 can be folded in the direction onto the first support arm 4. The first rotational axis 11 is arranged horizontally in this embodiment. FIG. 3 illustrates an intermediate position, in which the second support arm is only slightly deflected about the first rotational axis. FIG. 4 shows the stand in a so-called ready position, in which the support arms with the surgical microscope 2 are only slightly deflected out of the main body 3. FIGS. 5 and 6 finally illustrate the stand 1 in a parked position with a completely folded first support arm 4 and second support arm 5. In this case, the first support arm 4, the second support arm 5 and the surgical microscope 2 are held completely within a cavity 8 in the interior of the main body 3 and, as a result, are housed in a particularly protected and space-saving manner.

Figure 7:
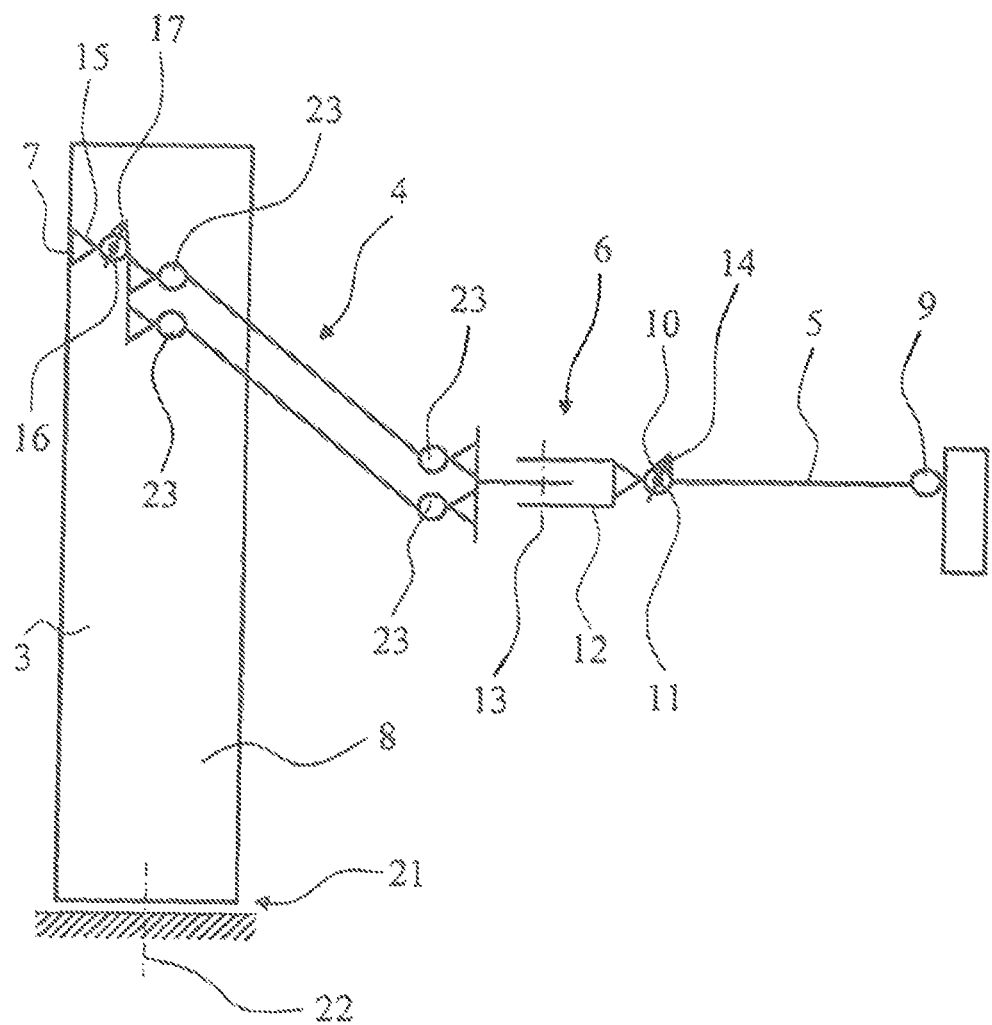
FIG. 7 is a schematic showing the kinematics of the stand In a work position.

The kinematics of the stand will be explained below on the basis of FIG. 7 to FIG. 9. FIG. 7 shows the stand 1 in a configuration in which the medical practitioner can use it during the surgical procedure or treatment.

The second support arm 5 is connected to the first support arm 4 via a first joint connection 6. The first joint connection 6 in this case comprises a first joint 10 with a first degree of freedom of motion which is configured as a rotational degree of freedom about, a first rotational axis 11, which is arranged horizontally. The first joint connection 6 furthermore comprises a second joint 12 with a second degree of freedom of motion which is configured as a rotational degree of freedom about a second rotational, axis 13. Here, the second rotational axis 13 is aligned skew, in particular orthogonal, with respect to the first rotational axis 11 and, more particularly, aligned vertically.

The first joint connection 6 furthermore has a first switching device 14, which can be put into a first switching state and into a second switching state and with the aid of which the rotational degree of freedom about the first rotational axis 11 of the first joint 10 is switchable. In this context, "switchable" means that the rotational degree of freedom can optionally be constrained or released. If the surgical microscope is required, during a surgical procedure, the first switching device is put into the first switching state, in which the rotational degree of freedom about the first rotational axis 11 of the first joint 10 is constrained, preferably blocked. This is how the surgical microscope can, during the surgical procedure, be aligned in the workspace described on the basis of FIGS. 1 and 2. However, if the stand with the surgical microscope should be transferred into a rest position, the first switching device is put into the second switching state, in which the rotational degree of freedom about the first rotational axis 11 of the first joint is opened such that a simple movement option is provided for transferring the stand from the operation configuration into the rest position.

In one embodiment of the invention, the first switching device 14 is configured in such a way that the rotational degree of freedom about the second rotational axis 13 of the second joint 12 is also switchable. In those operation phases in which the surgical microscope is required, the first switching device 14 is put into the first switching state, in which the second rotational axis 13 of the second joint 12 is opened such that the workspace of the stand, described on the basis of FIGS. 1 and 2, is available for the surgical procedure. However, if the stand with the surgical microscope 2 should be brought into a rest position, the first switching device is brought into the second switching state, in which the rotational degree of freedom about the second rotational axis 13 of the second joint is constrained, preferably blocked, such that a defined movement option is given, for transferring the stand from the operation configuration into the rest position. In particular, this at least largely avoids an undesirable movement of the second support arm 5 relative to the first support arm 4 during the transition into the rest position.

In a further embodiment (not illustrated), the positions of the first joint 10 and of the second joint 12 of the first joint connection 6 are interchanged.

The first switching device 14 can preferably only be put into the second switching state if a longitudinal axis of the first support arm 4 and a longitudinal axis of the second support arm 5 are arranged in one plane. Such positions of the stand are illustrated in FIG. 1. Hence, the stand can only be transferred into the ready or parked position from certain positions of the stand.

The first support arm 4, which is embodied as a parallelogram structure in this embodiment, is arranged on the side of the first joint connection 6 lying opposite to the second support arm. The first support arm 4 is, in turn, connected to the main body 3 of the stand via a second joint connection 7.

The second joint connection 7 comprises a third joint 15, which has a rotational degree of freedom about a third rotational axis 16. Here, the third rotational axis 16 is preferably aligned parallel to the first rotational axis 11 of the first joint 10 during the transition of the stand into the rest position. In this embodiment, the third rotational axis 16 and the first rotational axis 11 are moreover arranged orthogonal to a longitudinal axis of the main body 3 during the transition such that the first, support arm 4 and the second support arm 5 can, in a particularly space-saving manner, be folded on top of one another and along the longitudinal axis of the main body 3. The second joint connection 7 was found to be particularly advantageous in combination with an embodiment of the first support arm 4 as a parallelogram structure since it allows an alignment of the first support arm 4 in a parked position along a longitudinal axis of the main body 3. This could not be realized in the case of a direct connection of the parallelogram joints 23 to the main body 3 in a plane parallel to the longitudinal axis thereof.

Furthermore, the second joint connection 7 comprises a second switching device 17, which can be put into a third switching state and into a fourth switching state, wherein, in the third switching state, the rotational degree of freedom about the third rotational axis 16 of the third joint 15 is constricted, preferably blocked, and wherein, in the fourth switching state, the rotational degree of freedom about the third rotational axis 16 of the third joint is open. The first switching device 14 and the second switching device 17 are preferably coupled to one another. Here, during a use of the surgical microscope, the first switching device 14 is put into the first switching state and the second switching device 17 is put into the third switching state. By contrast, when the stand is transferred into the rest position, the first switching device 14 is switched into the second switching state and the second switching device 17 is switched into the fourth switching state.

In an alternative embodiment (not illustrated), the first support arm is connected to the main body without the interposition of a second joint connection. This simplifies the mechanical structure of the stand. This embodiment is particularly advantageous if the first support arm is embodied as a single arm and not as a parallelogram structure. In this case, a space-saving arrangement of the first support arm on or in the main body of the stand is also possible in the parked position without a second joint connection.

The switching devices (14, 17) can be realized in various ways. Mechanical structures which are based on a force fit between individual joint bodies are feasible and can, for example, be embodied as a pin, which can be introduced into openings or grooves in the various joint bodies such that a relative movement between the joint bodies is blocked. Furthermore, mechanical solutions are conceivable which are based on friction between the joint bodies. As an example of this, reference is made to a brake, which can be triggered mechanically, electrically, hydraulically or pneumatically. Furthermore, a switching device can also foe realized by a switchable magnetic or electric field, which acts between the joint bodies.

Figure 8:
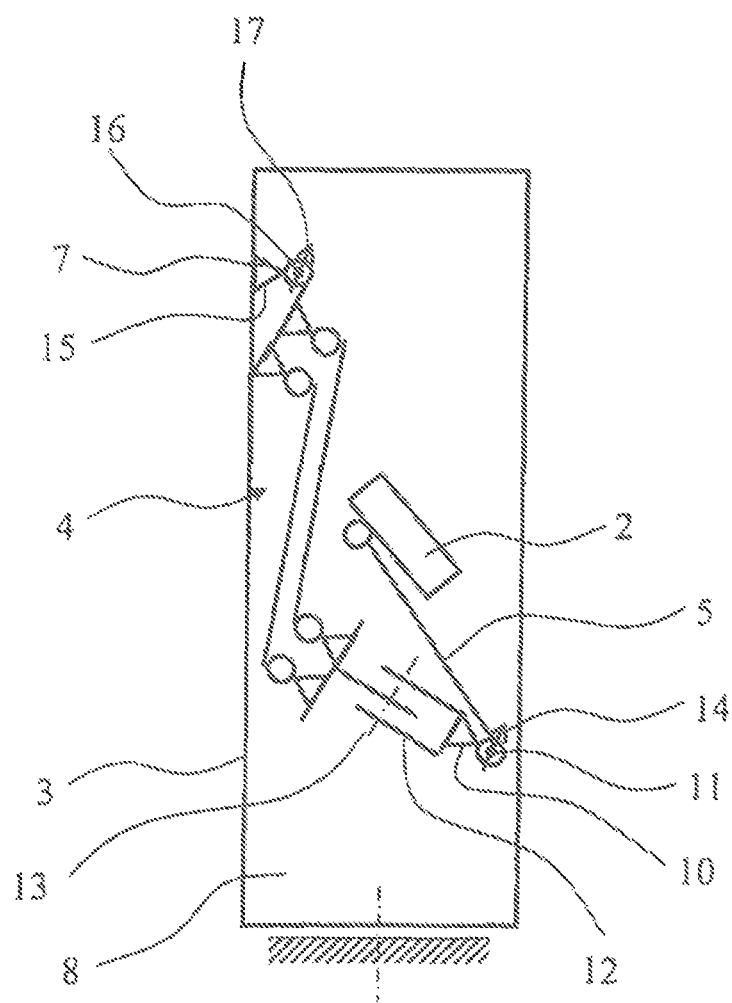
FIG. 8 is a schematic showing the kinematics of the stand in a parked position.

FIG. 8 illustrates the stand 1 in the parked position. In this position, the first switching device 14 is put into the second switching state and the second switching device 17 is put into the fourth switching state. As a result, it is possible to fold the first support arm 4 and the second support arm 5 over one another in a particularly space-saving manner and to stow them away in a cavity 8 in the interior of the main body 3 of the stand.

Figure 9:
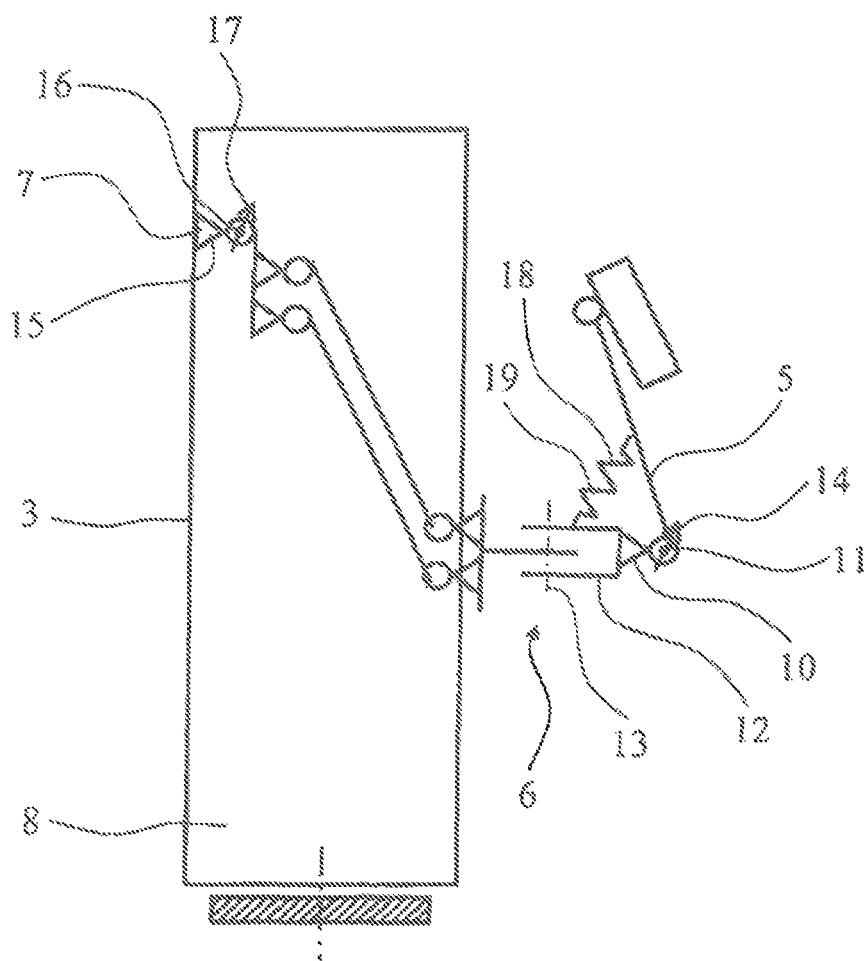
FIG. 9 is a schematic showing the kinematics of the stand in a ready position.

FIG. 9 shows the stand 1 in a ready position. The ready-position constitutes an intermediate position between the parked position and a work position during the use of the surgical microscope. In the ready position, the stand is held by a holding device 18 in a defined stable equilibrium state, from which it can only be moved by overcoming a holding force or a holding torque.

In an exemplary fashion, the holding device 18 in this embodiment has an energy store in the form of a tension/compression spring 19, which is arranged over and past the first joint 10 of the first joint connection 6 and in which a minimum of spring energy is stored in the shown position. In order to transfer the stand 1 from the ready position into a work position, in which the medical practitioner can use the surgical microscope during the surgical, procedure, the second support arm 5 is guided into the work position against the resistance of the tension/compression spring 19 and the rotational degree of freedom about the first rotational axis 11 of the first joint 10 is subsequently blocked with the aid of the first switching device 14.

In the embodiment shown in FIG. 9, the rotational degree of freedom about the third rotational axis 16 of the third joint 15 is blocked in the ready position. In an alternative embodiment (not illustrated), the second switching device 17 is switched in the ready position in such a way that the rotational degree of freedom about the third, rotational axis 16 of the third joint 15 is opened. In a still further embodiment, a further holding device is provided over and past the third joint between the main body and the first support arm. In further embodiments, a holding device is arranged over the whole first joint connection and/or over and past the whole second joint connection. The holding devices can in each case be embodied as energy store or, alternatively, as an electric motor.

Figure 10:
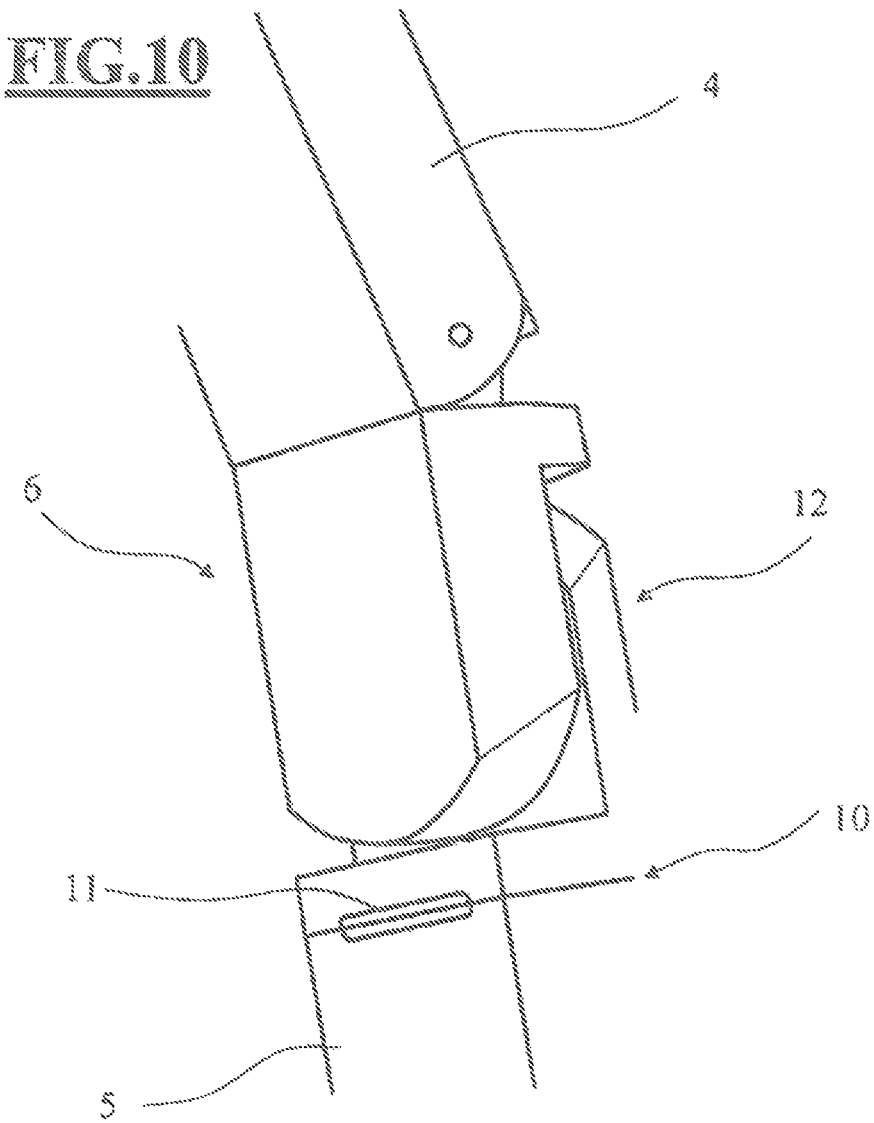
FIG. 10 is a detailed view of a first joint connection.

FIG. 10 illustrates a structural solution of the first joint connection 6. The first joint 10, which is embodied as a folding joint with a first rotational axis 11 arranged horizontally on the top side, and the second joint 12 with a second rotational axis can clearly be identified.

Figure 11:
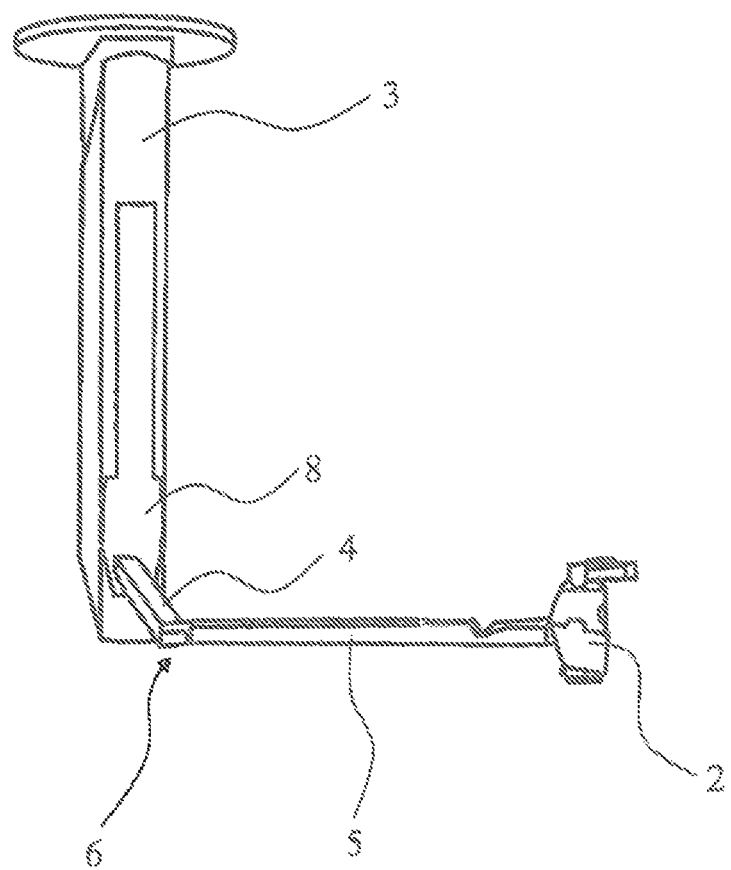
FIG. 11 shows an embodiment as a ceiling stand.
Figure 12:
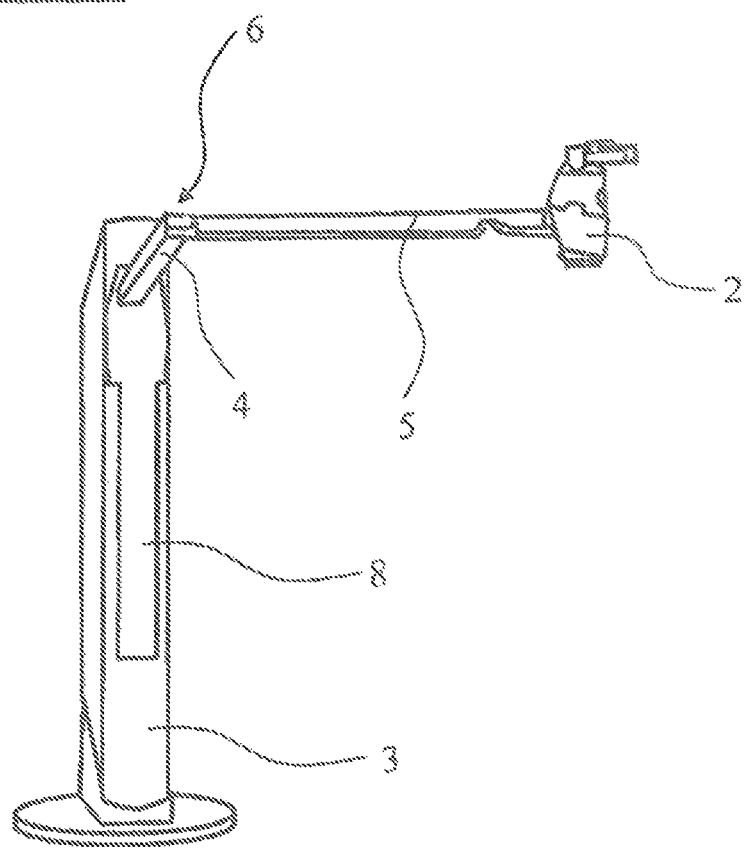
FIG. 12 shows an embodiment as a floor stand.
Figure 13:
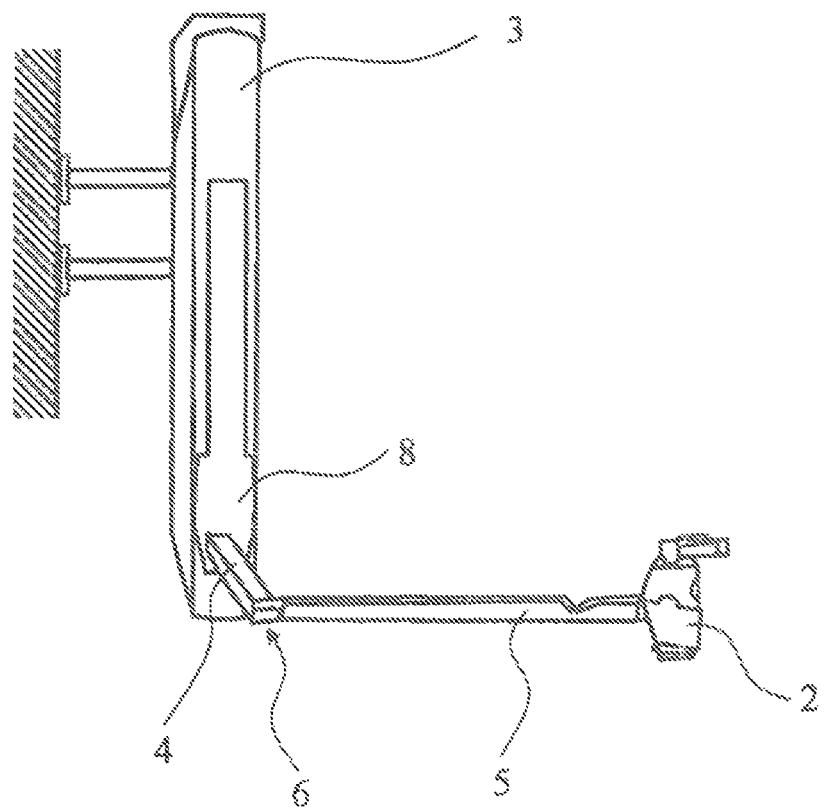
FIG. 13 shows an embodiment as a wall stand.

The stand can be embodied as a ceiling stand, floor stand or wall stand. Corresponding embodiments are shown in FIGS. 11 to 13. The main body 3 of the stand preferably has a cavity 8, which is embodied in such a way that the support arms and a surgical microscope attached to the second support arm can be stowed within an external contour of the main body 3 in the parked position. In this manner, the surgical microscope 2 is well protected in the parked, position and the risk of an inadvertent collision between the operating staff and the stand or the surgical microscope is reduced.

The stand preferably has a locking device, by means of which the support areas and/or the surgical microscope can be locked in the parked position. This prevents the support arms from inadvertently "falling out" of the main body 3. The embodiment of the main body 3 with a cavity is particularly advantageous in combination with the presented kinematics of the support arms since this enables a transfer of the stand from a work position into the volume, restricted due to the cavity, within a certain workspace and, in particular, along a defined movement trajectory such that the risk of a collision of the support arms (4, 5) or of the surgical microscope 2 with the main body 3 is reduced during the transition into the ready position or the parked position. The cavity 8 of the main body 3 can be viewed separately in conjunction with the support arms and the joint connections without the switching devices.

FIG. 14 illustrates a closure device 20 in the form of a sliding door, by means of which the opening of the cavity 8 can be closed in the parked position. As a result, the support arms (4, 5) and the surgical microscope 2 are protected against environmental influences and from being damaged.

The stand according to the invention is suitable for holding a plurality of medical instruments. A use in combination with a surgical microscope is particularly advantageous since these are often only used temporarily in many surgical procedures or treatments such that there often is a need for a change between a work position and a rest position. As a result of the embodiment with a switching device, provision is made overall for a stand which can be operated in a particularly ergonomic fashion, the workspace of which can be adapted to the particular requirements of a given situation. The invention is described herein on the basis of a stand with two support arms. However, the concept of the invention, of the switchable joint connections for adapting a workspace to the particular requirements during a surgical procedure can readily also be applied to stands with fewer or more support arms connected in series and/or in parallel.

It is understood that the foregoing description is that of the preferred embodiments of the invention and that various changes and modifications may be made thereto without departing from the spirit and scope of the invention as defined in the appended claims.

What is claimed is:

1. A stand for a medical device, the stand comprising:
   a first support arm;
   a second support arm configured to accommodate the medical device thereon;
   a first joint connection configured to connect said second support arm to said first support arm with a first degree of freedom of motion;
   said first joint connection having a first switching device configured to be transferable into a first switching state wherein said first degree of freedom of motion is disabled and into a second switching state wherein said first degree of freedom of motion is enabled;
   said first joint connection being configured to have a second degree of freedom of motion; and,
   said second degree of freedom of motion being enabled in said first switching state of said first switching device and said second degree of freedom of motion being disabled in said second switching state of said first switching device.

2. The stand of claim 1, wherein;
   said first support arm defines a first longitudinal axis and said second support arm defines a second longitudinal axis; and,
   said first switching device includes means for permitting said first switching device to be switchable only in said second switching state when said first longitudinal axis of said first support arm and said second longitudinal axis of said second support arm are disposed in one plane.

3. The stand of claim 2, wherein said first degree of freedom of motion of said first joint connection is configured as a translational degree of freedom along said first longitudinal axis of said first support arm.

4. The stand of claim 2, wherein said first degree of freedom of motion of said first joint connection is configured as a rotational degree of freedom about a first rotational axis.

5. The stand of claim 4, wherein said second degree of freedom of motion is configured as a rotational degree of freedom about a second rotational axis.

6. The stand of claim 5, further comprising:
   a main body; and,
   a second joint connection configured to connect said first support arm to said main body with a rotational degree of freedom about a third rotational axis.

7. The stand of claim 6, wherein said first and third rotational axes are arranged so as to be parallel to each other.

8. The stand of claim 6, wherein said second joint connection includes a second switching device configured to be transferable into a third switching state wherein the rotational degree of freedom about said third rotational axis is disabled and into a fourth switching state wherein the rotational degree of freedom about said third rotational axis is enabled.

9. The stand of claim 8, wherein said first switching device and said second switching device are coupled.

10. The stand of claim 9, wherein said rotational degree of freedom about said third rotational axis of said second joint connection is disabled when the first degree of freedom of motion of the first joint connection is disabled and the rotational degree of freedom about said third rotational axis of the second joint connection is enabled when the first degree of freedom of motion of the first joint connection is enabled.

11. The stand of claim 6, further comprising a switchable coupling between said main body, said first support arm and said second support arm and configured to cause a movement of said first support arm relative to said main body to be coupled to a movement of said second support arm relative to said first support arm.

12. The stand of claim 6, wherein said main body has a cavity wherein said first support arm and said second support arm can be accommodated in a parked position of said stand.

13. The stand of claim 12, wherein said first switching device is transferred into said second switching state when said stand is positioned in said parked position.

14. The stand of claim 13, further comprising a latching device for latching at least one of said first support arm and said second support arm relative to said main body in said parked position.

15. The stand of claim 12, said stand further comprising a closure device configured so that said cavity can be closed.

16. The stand of claim 1, wherein said first support arm is configured as a parallelogram structure.

17. The stand of claim 1, further comprising a holding device configured to hold said first support arm and said second support arm in a ready position of the stand.

18. The stand of claim 17, wherein said first switching device is transferred into said second switching state in said ready position.

19. The stand of claim 18, wherein said holding device includes an energy store.

20. The stand of claim 19, wherein said energy store is configured as a spring.

21. The stand of claim 19, wherein said holding device includes a motor.

* * * * *

UNITED STATES PATENT AND TRADEMARK OFFICE
CERTIFICATE OF CORRECTION

PATENT NO. : 9,195,022 B2 
APPLICATION NO. : 13/959401 
DATED : November 24, 2015 
INVENTOR(S) : T. Miladinovic et al.

Page 1 of 1

It is certified that error appears in the above-identified patent and that said Letters Patent is hereby corrected as shown below:

In the specification,

In Column 1:
Line 16: delete "aria" and substitute -- arm -- therefor.

In Column 5:
Line 32: delete "at" and substitute -- a -- therefor.

In Column 7:
Line 35: delete "given," and substitute -- given -- therefor.

In Column 8:
Line 43: delete "foe" and substitute -- be -- therefor.

In Column 9:
Line 37: delete "areas" and substitute -- arms -- therefor.

In the claims,

In Column 12:
Line 17: delete "claim 19" and substitute -- claim 17 -- therefor.

Signed and Sealed this
Nineteenth Day of April, 2016

Michelle K. Lee
*Director of the United States Patent and Trademark Office*